United States Patent [19]

Johnston

[11] Patent Number: 4,637,401

[45] Date of Patent: Jan. 20, 1987

[54] VOLUMETRIC FLOW RATE DETERMINATION IN CONDUITS NOT DIRECTLY ACCESSIBLE

[76] Inventor: G. Gilbert Johnston, 417 S. 289th, Federal Way, Wash. 98003

[21] Appl. No.: 667,333

[22] Filed: Nov. 1, 1984

[51] Int. Cl.[4] .............................................. A61B 10/00
[52] U.S. Cl. .................................... 128/663; 128/713; 73/861.25
[58] Field of Search ................................ 128/656–658, 128/660–663, 713, 4; 73/861.25

[56] References Cited

U.S. PATENT DOCUMENTS

| | | |
|---|---|---|
| 3,347,224 | 10/1967 | Adams . |
| 3,359,974 | 12/1967 | Khalil . |
| 3,430,625 | 3/1969 | McLeod, Jr. . |
| 3,443,433 | 5/1969 | Liston et al. . |
| 3,542,014 | 11/1970 | Peronneau . |
| 3,726,269 | 4/1973 | Webster, Jr. . |
| 3,798,967 | 3/1974 | Gieles et al. . |
| 3,896,373 | 7/1975 | Zelby . |
| 3,938,502 | 2/1976 | Bom ..................................... 128/661 |
| 3,985,123 | 10/1976 | Herzlinger et al. . |
| 3,995,623 | 12/1976 | Blake et al. . |
| 4,024,873 | 5/1977 | Antoshikiw et al. . |
| 4,105,022 | 8/1978 | Antoshkiw et al. . |
| 4,142,412 | 3/1979 | McLeod et al. . |
| 4,232,373 | 11/1980 | Jackson et al. . |
| 4,237,729 | 12/1980 | McLeod et al. . |
| 4,259,870 | 4/1981 | McLeod et al. . |
| 4,299,226 | 11/1981 | Banka ..................................... 128/657 |
| 4,319,580 | 3/1982 | Colley et al. ......................... 128/661 |
| 4,329,993 | 5/1982 | Lieber et al. . |

FOREIGN PATENT DOCUMENTS

| | | | |
|---|---|---|---|
| 2758039 | 7/1979 | Fed. Rep. of Germany ...... | 128/663 |
| 0605608 | 5/1978 | U.S.S.R. ................................ | 128/656 |

OTHER PUBLICATIONS

Olson et al., "A Nondestructive Ultrasonic Technique To Measure Diameter and Blood Flow in Arteries", IEEE Transactions on Biomedical Engineering, vol. BME-21, No. 2, pp. 168-171, 3-1984
Martin et al., "An Ultrasonic Catheter for Intravascular Measurement of Blood Flow", IEEE Transactions on Sonics and Ultrasonics, vol. SU-27, No. 6, Nov. 1980, pp. 277-286.

Primary Examiner—Kyle L. Howell
Assistant Examiner—Ruth S. Smith
Attorney, Agent, or Firm—Christensen, O'Connor, Johnson & Kindness

[57] ABSTRACT

A catheter, particularly adapted for cardiac output determination, comprises an elongated tube of flexible material, the tube having a substantially rigid distal portion on which is disposed an ultrasonic transducer and a proximate, inflatable ballon. The ultrasonic transducer is arranged so as to direct a beam of ultrasound toward a transverse plane that bisects the balloon, and is connected by appropriate leads to a conventional Doppler circuit. With the balloon deflated, the signal from the Doppler circuit is sensed to measure blood velocity. Thereafter, the balloon is inflated so that it has a predetermined cross-sectional area in the transverse plane. The signal from the Doppler circuit is again sensed to measure blood velocity. Using a simple mathematical relationship, the effective internal cross-sectional area of the blood vessel is determined from the two measured velocities and from the predetermined cross-sectional area of the balloon when inflated. The volumetric flow rate is then determined by multiplying the first measured velocity by the effective internal cross-sectional area.

11 Claims, 8 Drawing Figures

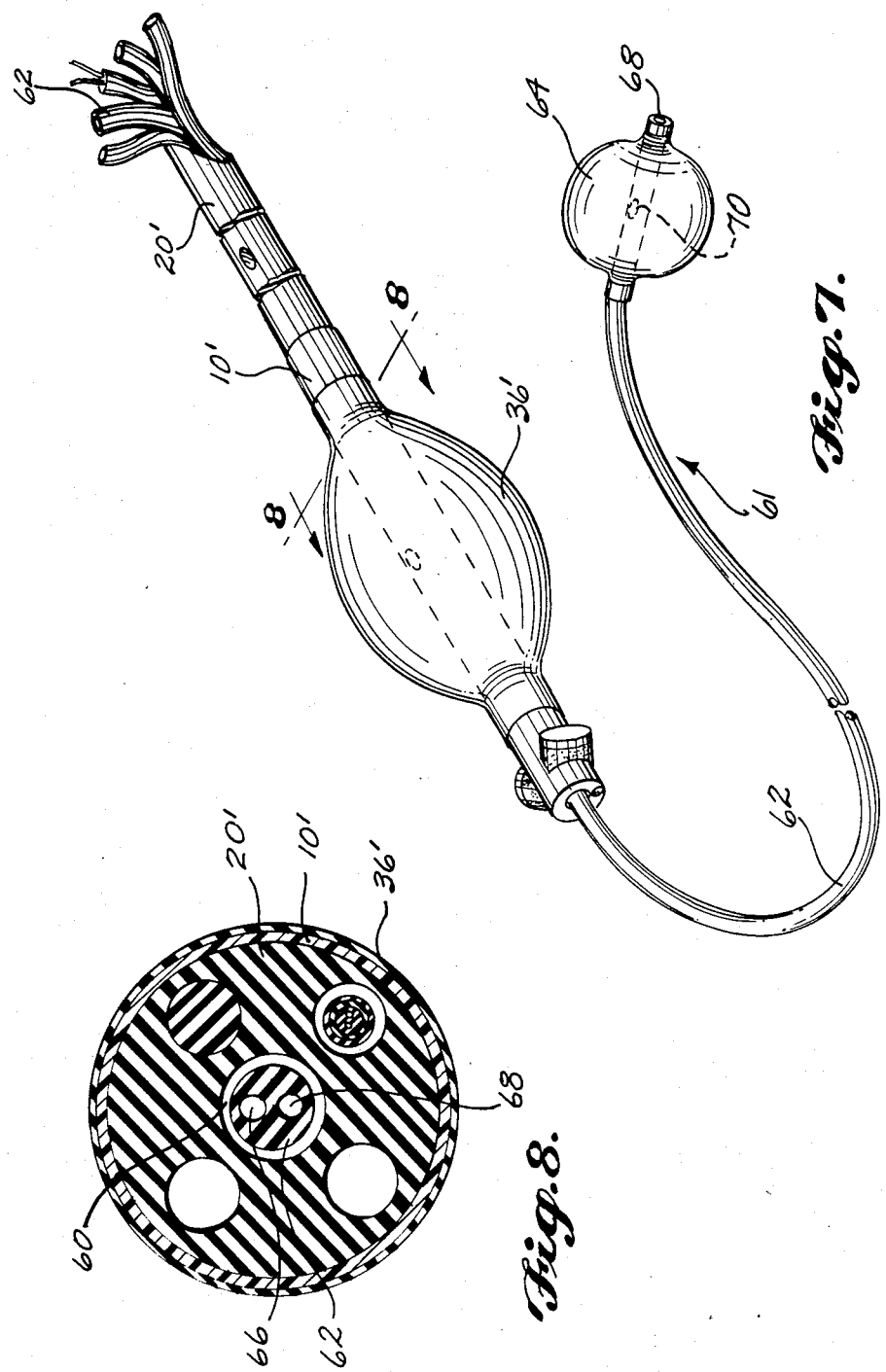

VOLUMETRIC FLOW RATE DETERMINATION IN CONDUITS NOT DIRECTLY ACCESSIBLE

FIELD OF THE INVENTION

This invention generally relates to apparatus for fluid flow determinations and, more particularly, to such apparatus that determine the volumetric flow rate of blood within, and the effective internal cross-sectional area of, portions of a biological circulatory system.

BACKGROUND OF THE INVENTION

Determination of the volumetric flow rate of fluid within a conduit that is not directly accessible is typified by the determination of cardiac output, i.e., the volumetric flow rate of blood in the pulmonary artery. Various methods have been commonly implemented in cardiac output determination and various other methods and apparatus have been proposed. The hallmark method is that expounded by Adolf Fick in 1870, and subsequently developed coincident with modern cardiac catheterization techniques. Blood samples are obtained from the pulmonary artery and from a systemic artery, and their oxygen content is measured. The consumption of oxygen per unit time, under steady state conditions, is either assumed or measured. Cardiac output is then calculated by dividing the oxygen consumption by the difference between the measured arterial and mixed-venous oxygen content. Unfortunately, the method is complicated, cumbersome to use, and yields poorly reproducible results.

Dye-dilution methods also have been used widely but are not considered to be significantly more accurate or precise. Such methods employ an indicator dye which is injected as a bolus into a blood vessel. Thereafter, the changing concentration of indicator dye is measured at a downstream site and plotted versus time. Cardiac output is then computed by integrating a portion under the resultant curve. Dye-dilution methods are hampered by problems of cumbersome apparatus, loss of indicator dye, recirculation of indicator dye, and anatomic circulatory shunts.

The problems of indicator dye loss and recirculation essentially were solved by the thermal dilution modification introduced by Fegler in 1953. In this method, a bolus of cold solution or "dye" is injected into the blood vessel through a proximal port of a multiple lumen catheter, and the subsequent "dilution" or changing blood temperature with time is measured downstream through the use of a thermistor located on the distal end of the catheter. The resultant concentration-time variation is electronically integrated and cardiac output computed therefrom. A representative catheter for use in thermal dilution methods can be seen in U.S. Pat. No. 3,736,269, Webster, Jr. In its most widely used form, this type of catheter also has an inflatable segment or balloon which is used as a flotation device to facilitate positioning of the catheter in the pulmonary artery. Reference, for example, U.S. Pat. Nos. 3,995,623, Blake et al., 4,024,873, Antoshkiw et al., 4,105,022, Antoshkiw et al., and 4,329,993, Lieber et al. Thermal dilution methods have proven, however, to be no more accurate than the Fick method, require cumbersome apparatus, and yield information intermittently.

A plethora of additional methods and apparatus, all employing intravascular catheters or probes, have been proposed for cardiac output measurements. These include apparatus that determine cardiac output by measurement of the differential temperature that results from localized heating of the blood (U.S. Pat. Nos. 3,359,974, Khalil; 3,798,967, Gieles et al.); that use electromagnetic energy (U.S. Pat. No. 3,347,224, Adams); or that measure the conductivity of the blood (U.S. Pat. No. 3,896,373, Zelby). Yet another alternative technique determines cardiac output from balloon and arterial pressure signals obtained from a balloon catheter (U.S. Pat. No. 3,985,123, Herzlinger et al.).

Perhaps the most promising methods for cardiac output determinations are those utilizing a catheter bearing an ultrasonic transducer. Reference, for example, U.S. Pat. No. 3,430,625, McLeod, Jr., which discloses an intravascular catheter bearing a pair of ultrasonic transducers at its tip. The transducers are coupled with a Doppler circuit which applies a high-frequency electrical signal (typically in the mHz range) to one of the transducers so as to cause the transmission of ultrasonic energy therefrom. An electrical output signal from the other transducer, resulting from returns of the transmitted ultrasonic energy from the blood cells, is compared with the high-frequency electrical signal applied to the transmitting transducer to develop a Doppler signal that is representative of any frequency shift caused by relative movement between the blood cells and the catheter. The Doppler signal is therefore directly related to blood velocity. Improved apparatus of this type, using a single transducer for transmission and reception, can be seen in U.S. Pat. No. 3,443,433, Liston et al.

Blood velocity by itself is not sufficient to determine cardiac output because the concurrent effective internal cross-sectional area of the blood vessel must also be known. In the past, such determination of effective internal cross-sectional area has been accomplished by the use of transducer arrays and range-gating or signal-power ratio processing methods, all of which require intricate and meticulously constructed transducers as well as complex electronic processing units. Reference, in this regard, U.S. Pat. Nos. 3,542,014, Peronneau, 4,142,412, McLeod et al., 4,237,729, McLeod et al., 4,259,870, McLeod et al., and 4,232,373, Jackson et al. Although these methods are capable of providing superior accuracy and precision in the determination of cardiac output, the complexity and expense of the catheter and of the related signal processing apparatus has significantly limited their widespread commercial application.

It is therefore the principal object of the invention to provide an apparatus for volumetric flow rate determination, such as cardiac output determination, which employs a simply and inexpensively constructed catheter bearing an ultrasonic transducer that can be discarded after a single use and which requires minimal signal processing in the necessary concurrent determination of conduit effective internal cross-sectional area.

SUMMARY OF THE INVENTION

Briefly, the invention resides in a catheter for determining the volumetric flow rate of a fluid ina conduit whose effective internal cross-sectional area is unknown.

In its quintessential application, the catheter is specifically adapted to determine the volumetric flow rate of blood in an intravascular conduit, such as cardiac output in the pulmonary artery. Such a catheter includes:

an elongated tube composed of substantially flexible material and having a distal portion;

flow restriction means carried by the distal portion, the flow restriction means being selectively controllable between a first state in which the flow restriction means does not substantially restrict flow through a reference plane transverse to the longitudinal axis of the tube's distal portion when the catheter is in use and a second state in which the flow restriction means does substantially restrict flow through that reference plane when the catheter is in use; and, ultrasonic transducer means carried by the distal portion proximate the flow restriction means, the ultrasonic transducer means being constructed and arranged so as to transmit and receive ultrasonic energy along a beam axis that intersects the reference plane at points always external to the flow restriction means.

BRIEF DESCRIPTION OF THE DRAWINGS

The invention can best be understood by reference to the following portion of the specification, taken in conjunction with the accompanying drawings in which:

FIG. 7 is a pictorial view of another embodiment of the catheter, in combination with a conventional balloon catheter; and, FIG. 8 is a cross-sectional view taken along the line 8—8 in FIG. 7.

DESCRIPTION OF THE PREFERRED EMBODIMENT

Figure 1:
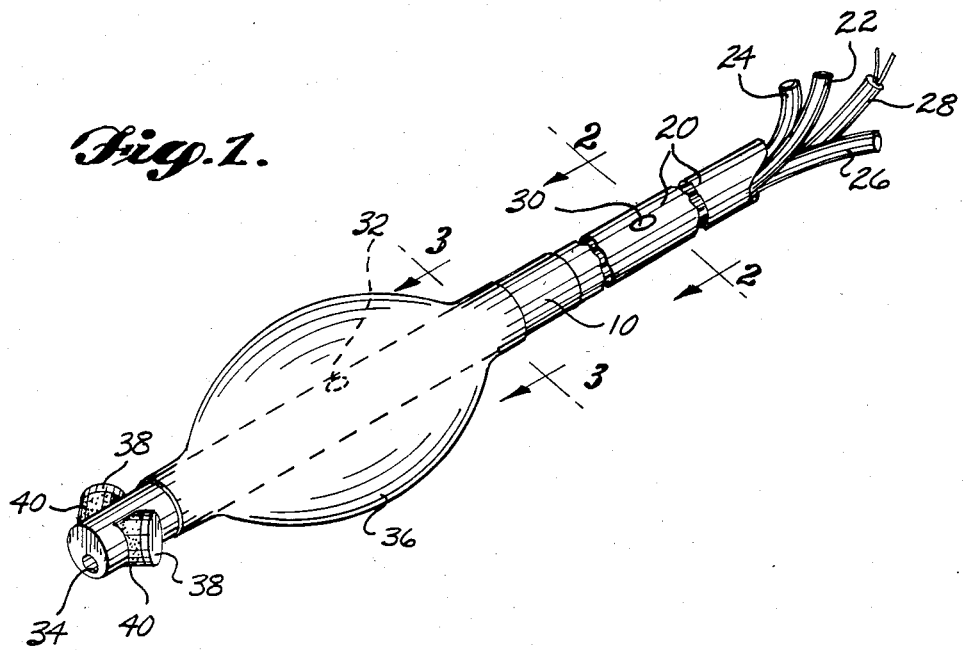
FIG. 1 is a pictorial view of a first embodiment of a catheter constructed according to the invention, particularly illustrating the distal portion thereof.
Figures 2, 3:
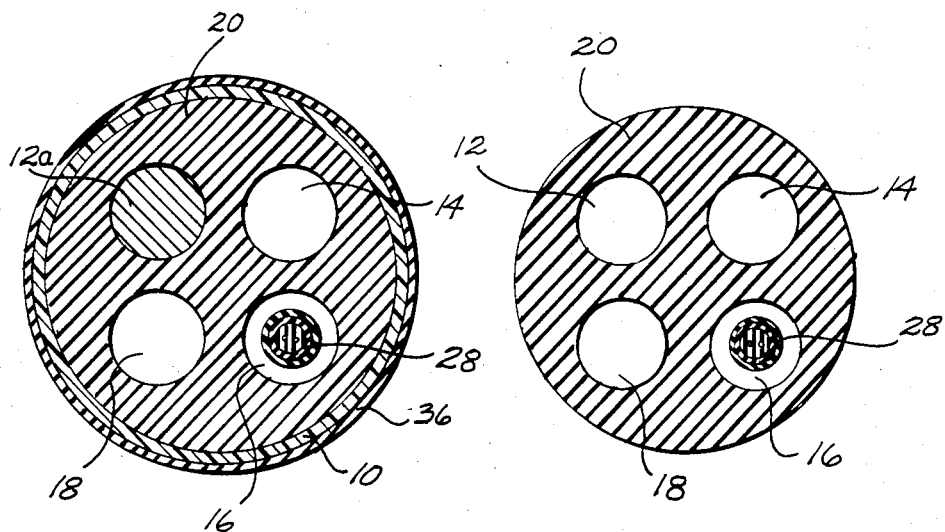
FIG. 2 is a cross-sectional view taken along the line 2—2 in FIG. 1.
FIG. 3 is a cross-sectional view taken along the line 3—3 in FIG. 1.

With reference now to FIGS. 1–3, the distal portion of one embodiment of the catheter is formed by a hollow, substantially cylindrical member 10 that is preferably fabricated from a rigid plastic material such as an acrylic and that is fitted over and secured in an appropriate manner to an elongated flexible tubing 20 having defined therein a plurality of lumens 12, 14, 16 and 18. The proximal portion of the catheter is provided with a plurality of smaller-diameter, elongated flexible tubings 22, 24 and 26. A preferred material for tubings 20, 22, 24 and 26 is a standard medical grade of a flexible polyurethane or polypropylene. Tubings 22, 24 and 26 are fitted into or otherwise brought into sealed fluid communication with lumens 12, 14 and 18, respectively, and an insulated electrical cable 28 passes into and along lumen 16. Lumen 12 terminates in a port 30 disposed in the exterior surface of tubing 20 that is located approximately 30-35 cm. from the distal end of the catheter, lumen 14 terminates in a port 32 in the substantially cylindrical exterior surface of member 10 intermediate the proximal and distal ends thereof, and lumen 18 terminates in a port 34 disposed in the distal end of the catheter.

A balloon 36 is carried by member 10 so as to cover port 32, and the respective ends of balloon 36 are secured in any appropriate manner to the exterior surface of member 10 so as to provide a fluid-tight seal. Preferably, balloon 36 is composed of a flexible, expandable material such as a standard medical grade of Silastic ™ silicon rubber. At least one and preferably a pair of ultrasonic transducers 38 are disposed at the distal end of member 10 and secured thereto by appropriate adhesive material 40. Preferably, each ultrasonic transducer 38 includes a piezoelectric crystal, although various ceramic polymers can also be used. Suitable electrical connections (not illustrated) are made between the ultrasonic transducers 38 and the leads and shield of cable 28 resident within lumen 16. The transducers (and their connections) are covered with a layer of appropriate sealing material (not illustrated) such as an epoxy resin to provide an electrical and fluid seal. Finally, each of the lumens 12, 14 and 16 is filled with an appropriate sealing material, from a point along its length beyond which the lumen is no longer required to the distal end of the catheter, as has been illustrated by sealing material 12a in lumen 12 (FIG. 3).

Figures 5, 6:
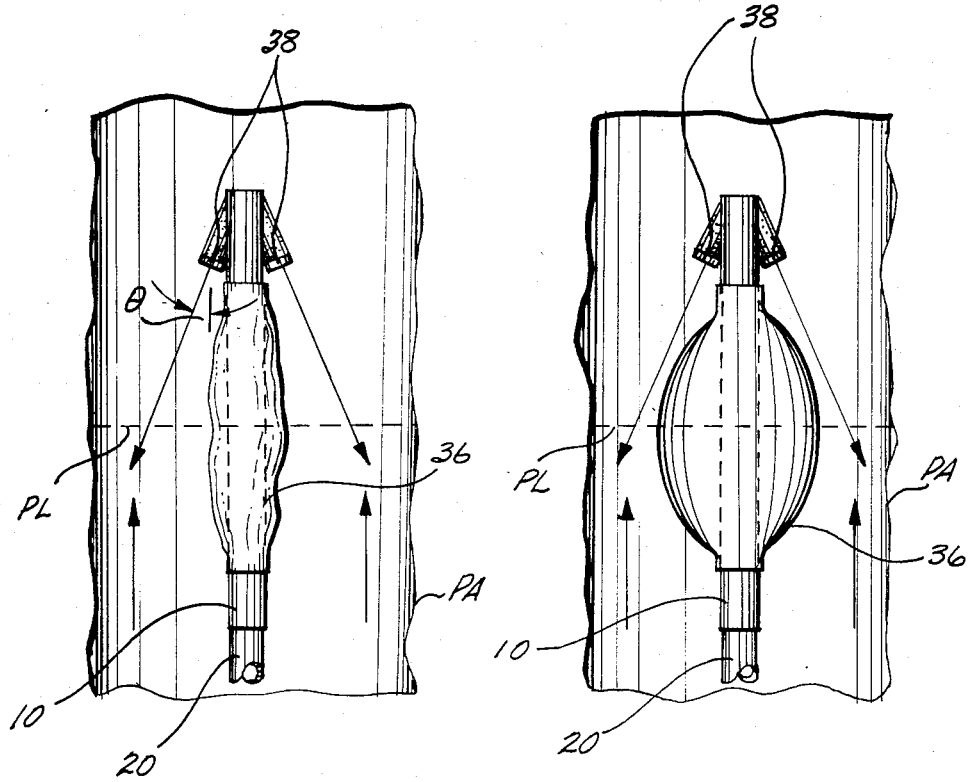
FIGS. 5 and 6 are elevational views of the catheter distal portion, as situated within a blood vessel during use.

As best illustrated in FIGS. 5 and 6, transducers 38 are mounted in diametrically opposing positions on member 10, and each transducer 38 is disposed so that its beam is directed toward the proximal end of member 10 and thus toward balloon 36. More specifically, the beam axis of each ultrasonic transducer is arranged at an angle $\theta$ with respect to the longitudinal axis of the catheter so as to intersect a plane PL transversely bisecting balloon 36 at the approximate midpoint thereof. Each beam axis must be unobstructed by balloon 36 not only when the balloon is unexpanded (FIG. 5) but also when the balloon is expanded (FIG. 6).

Figure 4:
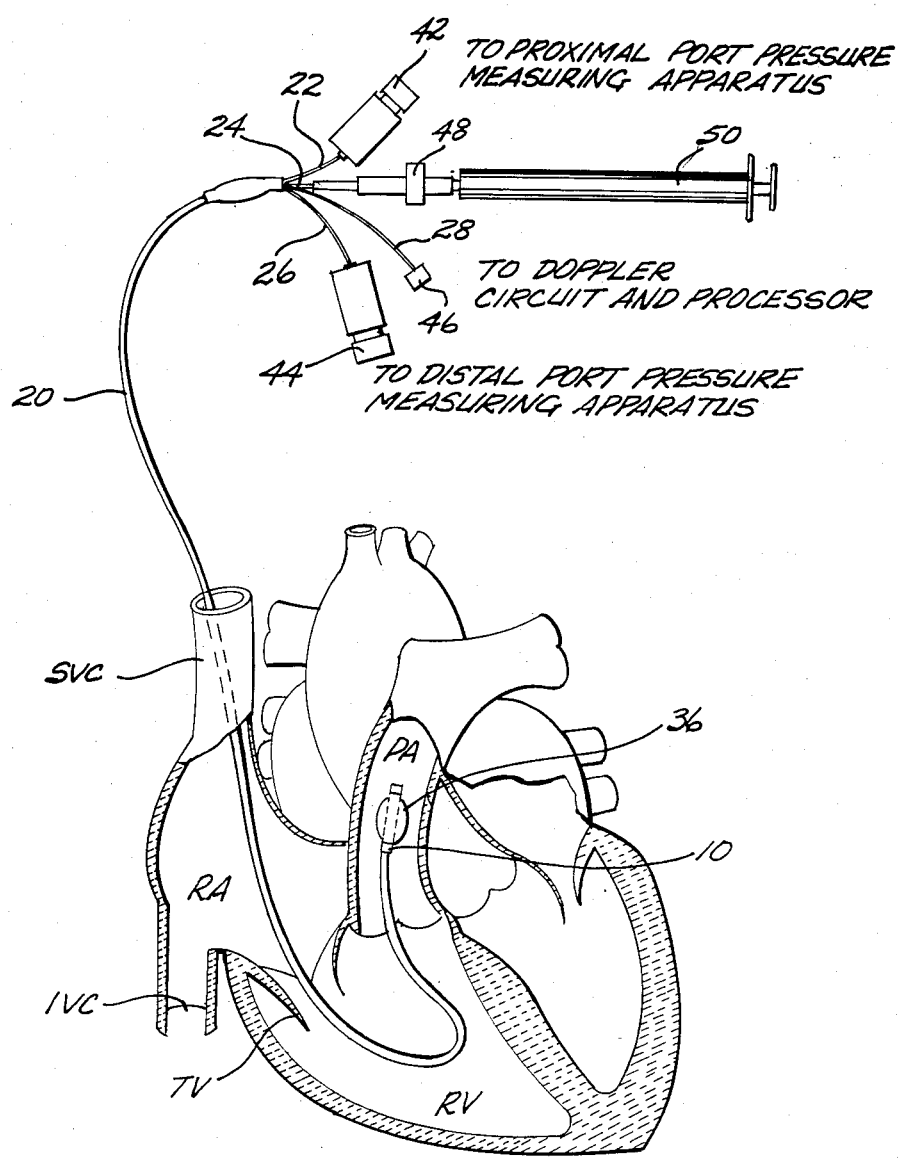
FIG. 4 is a pictorial view illustrating use of the catheter.

With additional reference now to FIG. 4, the distal end of the catheter is inserted into an appropriate vein and then advanced until it passes through the superior vena cava SVC, the right atrium RA, the tricuspid valve TV, the right ventricle RV, and into the main pulmonary artery PA. Tubing 22 going to the "proximal" port 30 is coupled to an appropriate pressure measuring apparatus by a connector 42, and tubing 26 going to the "distal" port 34 is connected to an appropriate pressure measuring apparatus by a connector 44. During the advancement of the catheter, pressure at either or both of these ports may be measured to assist in positioning of the catheter within the pulmonary artery PA. Cable 28 going to ultrasonic transducers 38 is coupled to a Doppler circuit and processor by an electrical connector 46. When the catheter has been appropriately positioned, the Doppler circuit applies a pulsed high-frequency electrical signal to the transducers which causes them to transmit ultrasonic energy. Reflected returns of the transmitted ultrasonic energy from objects within the beam of each transducer (e.g., blood cells moving within the main pulmonary artery PA) are detected by the ultrasonic transducers and result in a corresponding return signal that is used by the Doppler circuit to develop a Doppler signal representative of the velocity of the objects within the beams of the ultrasonic transducers. By appropriate signal processing techniques as are well known, the Doppler signal can be enhanced by the processor to eliminate artifact and noise so that the Doppler signal represents solely blood velocity within the main pulmonary artery PA.

Referring again to FIGS. 5 and 6, the blood velocity thus determined by the Doppler circuit is measured for the two conditions of balloon 36 illustrated. In FIG. 5, the balloon is substantially unexpanded and the cross-sectional area of the catheter within transverse plane PL is such so as to have no appreciable effect upon the blood velocity within the main pulmonary artery PA in the vicinity of plane PL. In FIG. 6, the balloon is substantially expanded so that the balloon has a predetermined and known cross-sectional area within transverse plane PL. One way to achieve such expansion is illustrated in FIG. 4, in which a syringe 50 containing a predetermined volume of fluid has been inserted into a connector 48 coupled to tubing 24, whereupon the fluid within syringe 50 may be injected into balloon 36 via tubing 24, lumen 14, and port 32 (FIGS. 1-3). Whatever the mechanism used to expand the balloon, the resultant cross-sectional area within plane PL must be known and must be such so as to significantly increase the blood velocity through the remaining, unrestricted portions of the pulmonary artery in the vicinity of plane PL.

Given that the blood velocity V for the unexpanded balloon condition illustrated in FIG. 5 and the blood velocity v for the expanded balloon condition illustrated in FIG. 6 have both been determined and recorded, and considering that the cross-sectional area a of the balloon when expanded is known, the effective internal cross-sectional area A of the main pulmonary artery PA can be easily determined by considering that the proportional relation:

$$\frac{v}{V} = \frac{A}{A - a} \quad (1)$$

can be rearranged as $$A = a\left(\frac{v}{v - V}\right) \quad (2)$$

Having thus determined the effective internal cross-sectional area A, the volumetric flow rate (or cardiac output) is easily determined by multiplication of the effective internal cross-sectional area A by the blood velocity V.

As can be readily appreciated, the catheter described can be simply and inexpensively constructed so as to permit one-time sterilization, use and disposal. If desired, automated apparatus can be provided for filling and emptying the balloon when measurements are to be made. In any event, the Doppler signal measurements and related determinations can be accomplished by a conventional Doppler circuit and a very simply programmed microprocessor.

Preferably, balloon 36 is hydrodynamically shaped so as to maintain the distal portion of the catheter centered within the blood stream and away from the walls of the pulmonary artery. To this end, the ends of balloon 36 are not rolled over on themselves during construction of the catheter, as is conventionally the case in the manufacture of other types of balloon catheters. There is still a distinct possibility, however, that the distal portion of the ctheter may lodge against one of the pulmonary artery walls, thereby substantially blocking blood flow on that side of the catheter. To avoid the resultant loos of velocity information that would result in such an event if a single ultrasonic transducer were used, the preferred embodiment contemplates as described the use of a pair of diametrically opposed transducers so that the beam of at least one of the transducers remains unobstructed at all times. Other transducer constructions are contemplated to avoid this problem, such as a ring-type transducer emitting a conical beam at the angle $\theta$ relative to the catheter longitudinal axis.

The proximal and distal ports 30, 34 may be used for purposes other than pressure measurements, such as the infusion and withdrawal of appropriate fluids. In fact, the principles of the invention can be applied to numerous catheter constructions such as the alternative embodiment illustrated in FIGS. 7 and 8, which is substantially identical to that previously described with the exception that tubing 20' includes an additional, central lumen 60 extending from its proximal end to its distal end. Lumen 60, which is larger in diameter than the remaining lumens in tubing 20', is used for the passage of a conventional balloon catheter 61 consisting of an elongated flexible tubing 62 that carries an inflatable balloon 64 on its distal portion. As best seen in FIG. 8, tubing 62 includes a pair of lumens 66 and 68, with lumen 66 terminating in a port 70 that is surrounded by balloon 64 and with lumen 68 terminating in the distal end of tubing 62.

In use, the catheter assembly in FIG. 7 is inserted into the venous system until the distal portion thereof is resident within the main pulmonary artery PA as illustrated in FIG. 4. Thereafter, the conventional balloon catheter 61 is further advanced an appropriate distance. When catheter 61 has been properly positioned, balloon 64 thereon is inflated (by injection of fluid into the balloon via lumen 66 and port 70) so as to create a wedge within the peripheral artery branch. As will be appreciated by those skilled in the art, measurements can be made concurrently of not only pulmonary artery pressure and cardiac output (as previously described) but also of pulmonary artery wedge pressure (by the use of an appropriate pressure measuring apparatus coupled to lumen 68 within catheter 61).

While the invention has been described with reference to a preferred embodiment, it is to be clearly understood by those skilled in the art that the invention is not limited thereto. For example, the rigidification of the catheter's distal portion afforded by member 10 is desirable to insure that the beam of each transducer 38 remains at a substantially constant angle relative to the catheter's longitudinal axis (and thus relative to balloon 36) during measurements. An alternate embodiment of the catheter would eliminate member 10 (wherein the transducers 38 and balloon 36 would be directly affixed to tubing 20) and would maintain the desired transducer/balloon relationship by appropriate design of those elements and choice of their materials or by the insertion of a relatively stiff yet flexible wire into one of the tubing lumens after the catheter's distal portion had been appropriately positioned in-situ.

Accordingly, the scope of the invention is to be interpreted only in conjunction with the appended claims.

The embodiments of the invention in which an exclusive property or privilege is claimed are defined as follows:

1. A catheter for use within an intravascular conduit, said catheter comprising:
   an elongated tube having a proximal portion of substantially flexible material and having a distal portion;
   flow restriction means carried by said distal portion of said tube, said flow restriction means being selectively controllable between a first state in which said flow restriction means does not substantially restrict flow through a reference plane transverse to the longitudinal axis of such distal portion when said catheter is in use in a location substantially fixed with respect to said reference plane and a second state in which said flow restriction means does substantially restrict flow through said reference plane when said catheter is in said location; and ultrasonic transducer means carried by said distal portion proximate said flow restriction means, said ultrasonic transducer means being constructed and arranged so as to transmit and receive ultrasonic energy along a beam axis that intersects said reference plane at points always external to said flow restriction means.

2. The catheter of claim 1, wherein said ultrasonic transducer means is distal relative to said flow restriction means.

3. The catheter of claim 2, wherein said ultrasonic transducer means is positioned adjacent the distal end of said tube.

4. The catheter of claim 1, wherein said ultrasonic transducer means includes a pair of ultrasonic transducers that are disposed in diametrically opposing positions on said distal portion of said tube.

5. The catheter of claim 1, further comprising control means carried by said tube, said flow restriction means including an expandable member carried by said distal portion of said tube, said control means being for selectively contracting and expanding said expandable member to achieve said first and said second states of said flow restriction means.

6. The catheter of claim 5, wherein said expandable member is hydrodynamically shaped when expanded so as to substantially center said distal portion of said tube in the conduit when said catheter is in use.

7. The catheter of claim 6, wherein said expandable member is a balloon and said control means includes a lumen defined within said tube that extends from the proximal end of said tube to the vicinity of said balloon and a port coupling said lumen to the interior of said balloon.

8. The catheter of claim 1, wherein said distal portion of said tube is substantially rigid.

9. The catheter of claim 8, further comprising a hollow, substantially cylindrical member of substantially rigid material that is fitted over and secured to said distal portion of said tube, and wherein said flow restriction means and said ultrasonic transducer means are secured to said hollow member.

10. The catheter of claim 1, wherein said tube has defined therein first and second lumens extending from the vicinity of the proximal end of said tube to said distal portion thereof, said first lumen terminating substantially at a first port in said tube that is proximal relative to said flow restriction means and said ultrasonic transducer means and said second lumen terminating substantially at a second port in said tube that is distal relative to said flow restriction means and said ultrasonic transducer means.

11. The catheter of claim 1, wherein said tube has defined therein a lumen extending from the vicinity of the proximal end of said tube to said distal portion thereof, said lumen terminating in a port in the distal end of said tube and being constructed so as to permit the passage therethrough of a balloon catheter.

* * * * *